(12) United States Patent
Schiemann

(10) Patent No.: US 9,700,383 B2
(45) Date of Patent: Jul. 11, 2017

(54) BRACKET SYSTEM AND METHOD FOR PLANNING AND PRODUCING A BRACKET SYSTEM FOR THE CORRECTION OF TOOTH MALPOSITIONS

(75) Inventor: Christian Schiemann, Neusass (DE)

(73) Assignee: Sirona Dental Systems GMBH, Bensheim (DE)

( * ) Notice: Subject to any disclaimer, the term of this patent is extended or adjusted under 35 U.S.C. 154(b) by 358 days.

(21) Appl. No.: 13/030,262

(22) Filed: Feb. 18, 2011

(65) Prior Publication Data
US 2011/0207072 A1     Aug. 25, 2011

(30) Foreign Application Priority Data
Feb. 22, 2010  (DE) .................. 10 2010 002 206

(51) Int. Cl.
*A61C 3/00*     (2006.01)
*A61C 7/00*     (2006.01)
(Continued)

(52) U.S. Cl.
CPC .............. *A61C 7/002* (2013.01); *A61B 6/14* (2013.01); *A61C 7/145* (2013.01); *A61C 7/146* (2013.01);
(Continued)

(58) Field of Classification Search
CPC .. A61C 7/12; A61C 7/125; A61C 7/14; A61C 7/141; A61C 7/143; A61C 7/145; A61C 7/146; A61C 7/148; A61C 7/16; A61C 7/18; A61C 7/20; A61C 7/22; A61C 7/28; A61C 7/282; A61C 7/285;
(Continued)

(56) References Cited

U.S. PATENT DOCUMENTS 3,469,314 A * 9/1969 Pearlman ............... A61C 7/12
                                                        433/8
3,721,005 A * 3/1973 Cohen ...................... A61C 7/14
                                                        433/16
(Continued)

FOREIGN PATENT DOCUMENTS

DE        698 37 353 T2      12/2007
EP        1 421 914 B1        3/2007
JP              241149     *  2/1990

OTHER PUBLICATIONS

English-language translation of official examination report dated Sep. 13, 2010 issued in German counterpart application—4 pages.
(Continued)

*Primary Examiner* — Yogesh Patel
(74) *Attorney, Agent, or Firm* — Fitzpatrick, Cella, Harper & Scinto

(57) ABSTRACT

The invention relates to a method for planning a bracket system (1) for the correction of malpositions of teeth (2), comprising a plurality of brackets (3) and an arch (4) wherein at least one platelet (6) per tooth is mounted on certain tooth surfaces (5) of the teeth to be corrected (2), a three-dimensional optical image (50) of the tooth region to be treated is created, the platelets (6) have registration elements (10) comprising registration points (11) and the registration points (11) have a characteristic form for registration in the three-dimensional optical image (50).

28 Claims, 5 Drawing Sheets

(51) Int. Cl.
  *A61C 7/14* (2006.01)
  *A61C 9/00* (2006.01)
  *A61B 6/14* (2006.01)
  *A61C 7/16* (2006.01)
  *G05B 19/27* (2006.01)

(52) U.S. Cl.
  CPC .............. *A61C 7/16* (2013.01); *A61C 9/0053* (2013.01); *G05B 19/27* (2013.01); *G05B 2219/37355* (2013.01)

(58) Field of Classification Search
  CPC ........... A61C 7/287; A61C 7/30; A61C 7/303; A61C 7/306; A61C 7/34; A61C 7/36
  USPC ...................... 433/8–17, 24, 72, 75
  See application file for complete search history.

(56) References Cited

U.S. PATENT DOCUMENTS

| | | | |
|---|---|---|---|
| 5,133,660 A * | 7/1992 | Fenick | 433/76 |
| 6,621,491 B1 * | 9/2003 | Baumrind et al. | 345/419 |
| 6,947,038 B1 * | 9/2005 | Anh | G06T 17/10 |
| | | | 345/419 |
| 7,133,042 B2 * | 11/2006 | Anh | G06T 17/10 |
| | | | 345/419 |
| 7,722,354 B1 * | 5/2010 | Dumas | 433/8 |
| 8,152,519 B1 * | 4/2012 | Dumas | A61C 7/14 |
| | | | 433/10 |
| 2004/0029068 A1 | 2/2004 | Sachdeva et al. | 433/24 |
| 2005/0239013 A1 | 10/2005 | Sachdeva | 433/24 |
| 2005/0244790 A1 * | 11/2005 | Kuperman | 433/213 |
| 2007/0141525 A1 * | 6/2007 | Cinader, Jr. | A61C 7/146 |
| | | | 433/23 |
| 2007/0231767 A1 * | 10/2007 | Sears et al. | 433/8 |
| 2007/0254257 A1 * | 11/2007 | Sachdeva | 433/9 |
| 2008/0145812 A1 | 6/2008 | Taub et al. | 433/3 |
| 2008/0153050 A1 | 6/2008 | Taub et al. | 433/3 |
| 2011/0294090 A1 | 12/2011 | Jung | 433/68 |

OTHER PUBLICATIONS

European Search Report dated Apr. 29, 2013.
Machine English translation of the European Search Report.

* cited by examiner

BRACKET SYSTEM AND METHOD FOR PLANNING AND PRODUCING A BRACKET SYSTEM FOR THE CORRECTION OF TOOTH MALPOSITIONS

TECHNICAL FIELD

The invention relates to a bracket system and a method for planning this bracket system for the correction of malpositions of teeth, which bracket system comprises a plurality of brackets and an arch.

STATE OF THE ART

A problem of erroneous bonding often occurs with the use of known bracket systems. In such systems, the brackets are not precisely bonded to the patient's teeth at the ideal positions intended for the brackets so that the treatment cannot achieve its goal in the desired manner.

A number of solutions for preventing the possibility of erroneous bonding are known in the prior art.

One option is the so-called indirect bonding of the brackets to the patient's teeth by means of transfer trays. First, a master model of plaster is made based on an impression. Thereafter, the master model is duplicated and a dental arch is made from plaster. The dental arch is removed from a silicone duplicating mold, and the individual teeth are cut by means of a diamond disk from the tip of the root up to just before the contact point, the stumps are ground off conically and doused with liquid wax. Furthermore, vertical channels are milled into the plaster so as to extend centrally along the teeth for the purpose of ensuring precise positioning of the brackets. Duplicate models of both of the jaws are made and placed in an articulator. A dental technician then casts an ideal setup model that corresponds to the treatment goal by heating the wax according to the instructions of the dentist in charge. The brackets are then positioned. The brackets are bonded to the setup model. For this purpose, a model position is first sought, in which all brackets can be positioned in a single plane such that they do not interfere with the gingivae or the antagonistic teeth. After all the brackets have been bonded to the setup model, measuring elements are inserted into the slots on the brackets, and then the setup model is imaged by means of a stereoscopic camera providing a first image and a second image from an offset angle. A three-dimensional representation of the setup model comprising the brackets and the measuring elements is generated from these two images. The brackets are then carefully detached from the surfaces of the teeth and bonded by means of a water-soluble bonding agent to the master model exhibiting the malpositions of the patient's teeth. The vertical channels ensure precise positioning of the brackets. After all of the brackets have been transferred to the master model together with their measuring elements, additional images of the master model are created by a stereoscopic camera, and a three-dimensional representation is generated. The exact position of the brackets can be computed from the three-dimensional representation of the measuring elements. The measuring elements are then removed, and so-called transfer trays are produced for the transfer of the brackets onto the patient's teeth. A transparent silicone is often used as the material for the transfer trays. After the transfer trays have been separated from the master model and evaluated, they are removed and bonded together with the brackets to the patient's teeth. After the bonding agent has dried, the silicone transfer trays are removed.

A bonding robot (orthorobot) that attaches the brackets to the ideal positions on the setup model as determined therefor by software can be used as a development for improving the precision of the transfer method. However, the transfer of the brackets is still carried out using transfer trays.

The drawback of this method is that the transfer of the brackets by means of transfer trays is carried out manually by the dentist and is inaccurate. Erroneous positioning is due to the fact that the transfer trays are inadequately adapted by the dental technician to match the tooth surface, or they are deformed during removal from the master model, or they are incorrectly applied to the patient's teeth by the dentist.

A further known option is the so-called "incognito" positioning of the brackets. This form of treatment is an orthodontic correction of the teeth of esthetic value due to being completely hidden from view. The special brackets are attached lingually to the inner surface of the teeth. Each individual bracket is specially customized for the patient in a laboratory. The brackets are usually produced by means of a computer-controlled CAD/CAM technology. In particular, the brackets are produced with exactly fitting lingual surfaces customized for the respective patient.

Positioning of the brackets is usually carried out indirectly using transfer trays. For the purpose of repair work, the brackets are usually attached to the patient's teeth directly by free-bonding.

The drawback of this method is that positioning of the brackets by means of transfer trays is associated with the aforementioned problems.

A further known option for positioning the brackets is free bonding by the dentist after previously marking the distance of the bracket from the tip of the respective tooth.

The drawback of this method is that it is only possible to keep the distance of the bracket from the tip of the tooth and it is thus not possible to achieve precise three-dimensional positioning of the brackets in relation to the depth, the lateral distance, and the relative angle between the alignment of the bracket and that of the respective tooth.

It is therefore an object of the present invention to make it possible to achieve more precise positioning of the brackets on the patient's teeth in order to achieve the planned goal of treatment, namely total correction of the malpositions of the patient's teeth.

SUMMARY OF THE INVENTION

One object of the invention is a method for planning a bracket system for correction of malpositions of teeth, which bracket system comprises a plurality of brackets and an arch. At least one platelet for each tooth is attached to defined surfaces of the teeth to be corrected. A three-dimensional optical image of the tooth area to be treated is then created, for which purpose the platelets comprise registration elements having registration points that have a characteristic shape for the purpose of registration in the three-dimensional optical image.

The bracket system comprises a plurality of brackets, an arch, and a plurality of platelets. Unlike prior brackets, the platelets are first bonded to the respective labial or lingual tooth surfaces, the positions of the platelets are scanned in a three-dimensional optical image and a three-dimensional radiograph, and prior, conventional brackets are then provided with a recess on a bonding surface of the brackets, which recess matches the shape of the platelets. In the next step, the bonding surface of the prepared bracket is provided with a layer of bonding material, and the prepared brackets are positioned on the platelets and bonded to the tooth surface. As a result, more precise positioning of the brackets on the patient's teeth is achieved than when using the prior method.

The brackets form an anchor point for the mechanical movement of the teeth in the case of fixed appliances. A bracket is a device for accommodating the arch by means of retaining means in the form of a horizontal slot. The brackets are attached to the arch by the use of ligatures or pins. Buccal or labial brackets refer to brackets attached to the outer surface of the teeth, and lingual brackets refer to brackets disposed on the inner surface of the teeth. The brackets can be made of stainless steel, gold, ceramics, a composite material, or titanium. In many applications, the brackets have to slide along the arch. The frictional forces can be altered by means of the ligatures. The arch extends around the entire dental arch. Correction of the teeth is effected by means of a small force acting on the teeth, which force is derived from the resilient arch and is transferred to the patient's teeth by way of the bonded brackets.

A three-dimensional optical image can be created by means of an intraoral dental camera that produces a three-dimensional optical image of the patient's teeth to be treated, for example, by a triangulation method.

The platelets comprise registration elements comprising registration points that have a characteristic shape for the purpose of registration in the three-dimensional optical image. The registration points can have an arbitrary characteristic shape, for example, they can be in the form of protuberances or recesses.

An advantage of the method of the invention is that better positioning of the brackets on the patient's teeth is achieved than when use is made of the conventional methods described above, since the user only has to position the prepared brackets on the bonded platelets and can make no positioning errors in doing so. The probability of a successful treatment goal is consequently improved by the better positioning of the brackets.

An advantage of the method of the invention is that an already known bracket system can be kept, since any desired conventional brackets can be prepared according to the method of the invention.

Advantageously, in addition to the three-dimensional optical image, a three-dimensional radiograph of the tooth area to be treated can be created, for which purpose the registration elements comprising registration points and disposed on the platelets are such that they are sensitive to X-rays for the purpose of registration in the three-dimensional radiograph due to the registration points being made of a material that has an absorptivity for X-rays that significantly differs from that of the other material of the platelet.

The three-dimensional radiograph of the upper and lower jaw can be produced, for example, by means of Computed Tomography (CT) or Digital Volume Tomography (DVT). In DVT, two-dimensional images are produced as data sets for the computation of three-dimensional structures, while in the case of CT the imaging is based on one-dimensional detection. A digital volume tomograph comprises a rotating X-ray source and a CCD sensor that are rotated through 180° or 360° around the fixed patient. A number of individual two-dimensional summation images are produced during such rotation, and a three-dimensional model is computed from the individual images obtained. Tomograms in all spatial planes and three-dimensional views can be computed from the three-dimensional model.

Advantageously, a planning unit used for the computer-assisted planning of the bracket system combines the data of the three-dimensional optical image and the data of the three-dimensional radiograph by superimposing registration points of the registration elements in the three-dimensional optical image and the three-dimensional radiograph so that a precise positional relationship between the platelets and the optical three-dimensional image and the three-dimensional radiograph is determined.

The registration points can be located in the three-dimensional optical image and the three-dimensional radiograph by means of a matching process or pattern recognition, in which the image is scanned for a search pattern of the registration elements. The identification of the registration segments can also be carried out visually by a user by means of the planning unit. The planning unit can be a conventional computer comprising a monitor, a computer mouse, and a keyboard and on which the appropriate software is installed for processing the image data.

Advantageously, computer-assisted planning of the bracket system to be produced is carried out by means of the planning unit based on the superimposed three-dimensional optical image and the three-dimensional radiograph.

In particular, the position of the brackets on the patient's teeth and the shape of the elastic arch are determined when planning the bracket system so that the corrective forces caused by torsion or bending of the arch counteract the malpositions of the patient's teeth.

Advantageously, a virtual master model of the upper jaw and/or lower jaw is produced on the basis of the three-dimensional optical image, which virtual master model includes the malpositions of the patient's teeth. The individual teeth are corrected virtually by the user by means of the planning unit, and an ideal virtual setup model is produced in which all malpositions of the patient's teeth are corrected. Corrective positional changes of the individual teeth are computed from the deviations of the master model from the setup model, and the arrangement of the brackets and the arch of the bracket system are determined from these corrective positional changes of the individual teeth.

The advantage of this development of the invention is that the known method steps for bonding the brackets to the patient's teeth by means of transfer trays is carried out virtually with the aid of a computer, namely by the production of a master model and a corrected setup model. The necessary positional change of each individual tooth can then be computed automatically from the corrections made by the user, and planning of the bracket can be carried out automatically with the knowledge of the exact dimensions of the brackets and arch and the mechanical properties thereof.

A further advantage of this development is that a master model and a setup model need no longer be produced laboriously in the laboratory, and planning can be carried out by means of the planning unit immediately after the scan has been carried out on the dentist's premises, and the brackets can then be prepared by means of a CAD/CAM unit. Thus the treatment time is reduced significantly, and precision is improved over the conventional production of the models in the laboratory by such automation.

Advantageously, factors derived from the optical three-dimensional image, namely the spatial arrangement and shape of the teeth, and additional factors derived from the three-dimensional radiograph concerning the distribution of hard and soft tissue, namely the positions and dimensions of tooth roots in the apical basebone of a patient's jaw, the dimensions of the jawbone, the anatomical junctions, the shape of the gingivae, the, and/or the position of the palate can be allowed for in planning the bracket system. A probability of success in achieving the desired permanent mechanical positional changes of the patient's teeth according to the setup model can be computed from the arrangement of the hard and soft tissue by implementing the known material constants of the different types of tissue.

Knowing the mechanical properties of the different types of tissue and of the brackets and arch, such as the modulus of elasticity, modulus of torsion, compressive strength, tensile strength, and bending strength, the probability of success in achieving the positional changes of the individual teeth can be computed with the aid of a computer by means of a numerical simulation such as the so-called multibody simulation. In multibody simulation, real bodies are reproduced by means of a plurality of non-deformable bodies. Here, the growth direction of the skeletal bases of the viscerocranium and of the teeth can be allowed for, particularly in the case of children. The reactions of the jawbone or the tissue to the corrective forces are anisotropic so that the probability of success can be computed numerically.

Advantageously, alternative recommendations for treatment such as extracting, stripping, or operating can be proposed by the planning unit if the probability of success computed by the planning unit is too low.

If the computed probability of success is too low, the planning unit indicates that the treatment is not likely to give successful results and proposes alternative treatments. Extraction is the removal of a tooth without surgery. With stripping (approximal enamel reduction), the sides of the patient's teeth are ground slightly in order to gain space for the neighboring teeth. Surgery involves correction of the skeletal units (maxilla, mandible, alveolar processes) surgically corresponding to their malposition for the purpose of achieving an optimum positional relationship.

Advantageously, the user can input further individual treatment strategies, namely an arbitrary occlusal concept (e.g. Angle appliance, Andresen appliance, or a bioesthetic restoration), a case history of the respective patient, foreseeable growth development and/or a required overcompensation of the correction, and these can be allowed for when planning the bracket system.

For improving the treatment goal, individual treatment strategies can be inputted by the user and allowed for when planning the bracket system, by considering the merits of the different factors in relation to the mechanical stability of the ideal alignment of the teeth according to the setup model and the inputted treatment strategies. Most occlusal concepts such as bioesthetic restorations allow the lower buccal cusp tips to be occluded with the antagonistic grooves in the maxillary teeth. When preparing the digital setup, the user must mark the corresponding points, for example, the point of the mesial cusp of tooth #46 in accordance with the dental chart, and, for example, lead to the point on the marginal ridge of tooth #16. An overcompensation of the correction is primarily necessary in the case of a strongly rotated tooth that is derotated through more than 35°, for example. This overcompensation is required because the tooth turns back through approximately 5° to 10° on removal of the bracket system and completion of the tooth correction.

Advantageously, each platelet can comprise registration elements comprising at least three registration points.

Thus spatial orientation of the platelets in the three-dimensional optical image and the three-dimensional radiograph is made possible. The three registration points can be arranged as an equilateral triangle, for example.

Advantageously, prefabricated brackets can be adapted to the bonded platelets by means of a CAD/CAM unit after planning of the bracket system has been carried out by the planning unit, in that a recess is carved out of a bonding surface of each bracket so as to mate with the shape of the platelet such that the planned position of the bracket is achieved relative to the tooth when the respective bracket is attached to the corresponding platelet.

Thus automated, time-saving preparation of the brackets is made possible, this being less error-prone than manual adaptation by a dental laboratory assistant. The position of the recess is determined by the planning unit in that the planned position of the bracket on the tooth is set in relation to the position of the bonded platelet.

Advantageously, the prefabricated brackets can be adapted to the bonded platelet by means of a CAD/CAM unit, and the entire bonding surface of each bracket can be in the form of a counterpart to the respective tooth surface in order to give a perfect fit.

In addition to the production of a recess, the entire bonding surface of the bracket is machined such that it fits the tooth surface to be bonded. This makes better positioning of the bracket on the tooth possible, since the bracket bears exactly on the tooth surface and any tilting of the bracket that could result in erroneous positioning thereof is obviated.

The bonding surface may be coated with a layer of plastics material. This layer may then be machined to adapt the bracket to the tooth surface to be bonded. Thus the service life of the machining tool is increased over that achieved when the tool is used for machining metal.

Advantageously, the brackets can be bonded manually to the respective tooth surface by means of a bonding agent, once the brackets have been adapted to fit the respective tooth surface.

A special photopolymerizing two-component bonding agent can be used as bonding agent. During the bonding process, care must be taken to ensure that no air bubbles occur in the bonding layer and that the entire space between the bonding surface of the bracket and the tooth surface is filled with the bonding layer.

Advantageously, the tooth surfaces to be bonded can be labial and/or lingual tooth surfaces.

The appropriate buccal or lingual brackets are used depending on whether the bracket system is to be placed on the outer or inner surface of the teeth respectively.

The individual steps of the method of the invention can all be carried out by the dentist himself on his premises using the planning unit comprising a CAD/CAM unit. The bonding of platelets to the teeth prior to the registration can also be carried out by a dental assistant. The production of the virtual setup model based on special parameters defined by the dentist can also be carried out by the dental assistant. Only the insertion and bonding of the prepared brackets to the platelets should be carried out by the dentist himself.

A further object of the invention is a bracket system for the correction of malpositions of teeth, which bracket system comprises a plurality of brackets, an arch, and a plurality of platelets. The platelets comprise a bonding surface for bonding the same to a defined surface of a tooth to be corrected, and registration elements comprising registration points that have a characteristic shape for enabling registration in a three-dimensional optical image.

The bracket system of the invention is intended for carrying out the method defined in claim 1. The platelets comprise registration elements comprising registration points, the characteristic shape of which can be in the form of a protuberance or a recess in order to enable the registration points to be located in the optical three-dimensional images.

Advantageously, the registration elements comprising registration points can be sensitive to X-rays, for which purpose the registration points are of a material that has an absorptivity for X-rays that significantly differs from the absorptivity of the other material of the platelet in order to make registration in a three-dimensional radiograph possible.

Thus the registration points become visible on the three-dimensional radiograph and can be superimposed by the optical three-dimensional image of the registration points.

Advantageously, the brackets can comprise a recess that is in the form of a counterpart to the shape of the platelets in order to cause the platelet to precisely fit the respective bracket.

Thus the bracket can be placed on the matching platelet so that very precise positioning of the bracket on the tooth is achieved.

Advantageously, the brackets can comprise bonding surfaces that are each in the form of a counterpart of the surface of the tooth to be bonded in order to achieve a better fit of the bond.

Thus positioning of the bracket on the tooth is improved since the bracket lies exactly on a par with the tooth, as it rests exactly against the tooth surface.

BRIEF DESCRIPTION OF THE DRAWINGS

Exemplary embodiments of the invention are shown in the drawings, in which.

EXEMPLARY EMBODIMENTS

Figure 1:
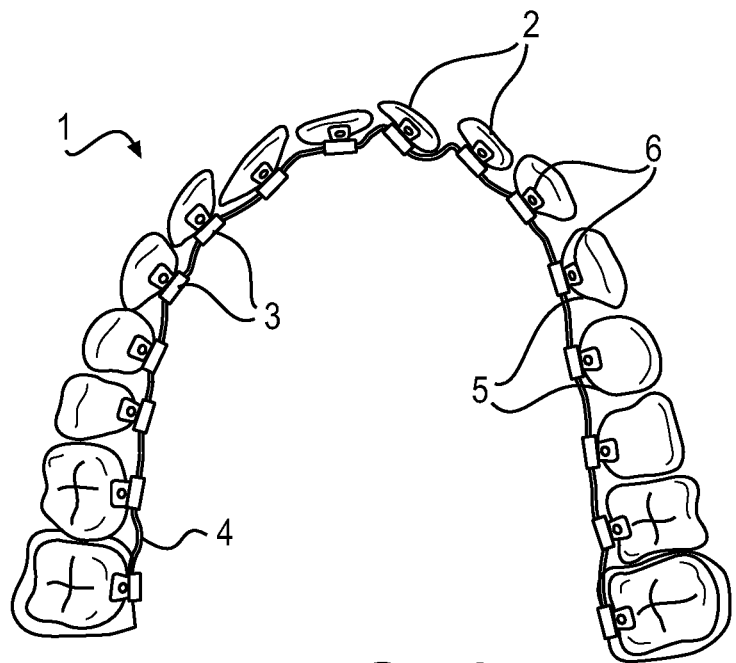
FIG. 1 is a sketch of a bracket system.

FIG. 1 is a sketch of the bracket system 1 for correcting malpositions of a patient's teeth 2. The bracket system 1 comprises a plurality of brackets 3 and an arch 4 extending along the inner surfaces of the row of teeth. An embodiment of the bracket system for the labial or buccal side of the patient's teeth 2 is likewise possible, for which purpose however, special buccal brackets are used. Platelets serving to position the brackets 3 are attached to the inner, lingual surfaces of the patient's teeth 2 to be corrected. The method for positioning the brackets is described below in greater detail.

The basic principle can be divided into the following steps: In the first step, the platelets 6 are bonded to the patient's teeth 2. In the second step, an optical three-dimensional image and, optionally, a three-dimensional radiograph of the patient's teeth together with the platelets 6 bonded thereto are created. The positions of the platelets 6 relative to the teeth are identified in the optical three-dimensional image based on the basis of registration elements that comprise registration points disposed on the platelets 6. In the next step, planning of the bracket system 1 is carried out by defining the positions of the individual brackets 3 and the shape of the arch 4. The locations at which the bonding surfaces of the brackets are to be prepared can be computed by the planning unit from the positions of the virtual brackets 3 and the defined positions of the platelets 6. In the final step, the prepared brackets 3 are then positioned on the platelets 6 and bonded to the lingual tooth surfaces.

Figure 2A:
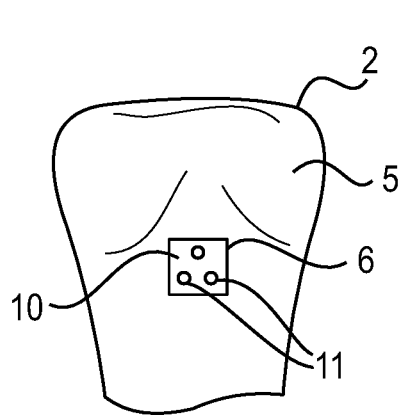
FIG. 2a is a sketch of a lingual tooth surface comprising a platelet.

FIG. 2a shows the lingual surface 5 of an incisor 2, to which the platelet 6 is bonded approximately centrally in the desired bonding region of the bracket. The platelet 6 comprises registration elements 10 having registration points 11 that have the shape of round spherical segments protruding from the plane of the platelet. They are particularly advantageous for the purpose of registration in a three-dimensional optical image.

Figure 2B:
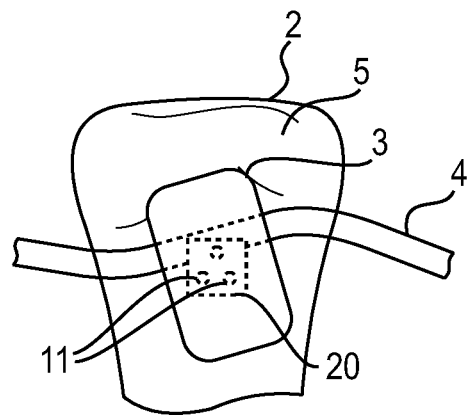
FIG. 2b is a sketch of the incisor shown in FIG. 2a in a further step of the method of the invention.

FIG. 2b is a sketch of the incisor 2 shown in FIG. 2a in a further step of the method of the invention. A prepared bracket 3 comprising a recess 20 that mates exactly with the platelet 6 is positioned on the platelet 6 comprising registration elements 11. Prior to bonding, the bracket 3 is coated with an adhesive layer that fills out the entire space between the bracket 3 and the lingual surface 5 of the tooth 2 during bonding. The arch 4 that exerts corrective forces such as torsional, tensile, and thrust forces on the incisor 2 to be corrected extends centrally through the bracket 3.

Figure 3:
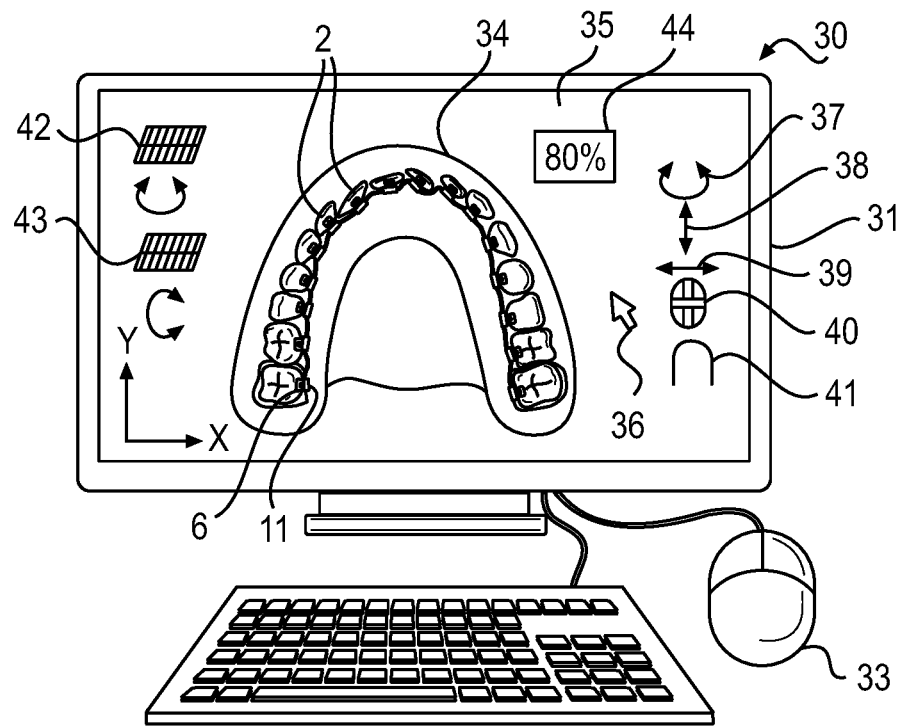
FIG. 3 shows an embodiment of the planning unit.

FIG. 3 shows an embodiment of the planning unit 30 comprising a video monitor 31, a keyboard 32, and a computer mouse 33. The monitor 31 shows a master model 34 produced from the data of the three-dimensional optical image 50 in combination with the data of a three-dimensional radiograph 51. For the purpose of superimposing the data of the three-dimensional optical image 50 and the data of the three-dimensional radiograph 51, use is made of the registration points 11 of the platelets 6, which can be registered both in the optical three-dimensional image on account of their characteristic shape and in the three-dimensional radiograph on account of their material composition showing a higher absorptivity for X-rays. A cursor 36 used for virtually machining the master model 34 is shown on the virtual worktop 35. Furthermore, a plurality of virtual tools are shown, namely, a first virtual tool 37 for rotating the virtual teeth 2 about their axes defined by the shape of the tooth roots, a second virtual tool 38 for displacing the virtual teeth 2 along the axes of the teeth 2, a third virtual tool 39 for displacing the virtual teeth 2 laterally in order to close possible gaps between the teeth, a fourth virtual tool 40 representing the model of a bracket 3 that can be selected individually for every tooth, and a fifth virtual tool 41 representing a model of the arch 4. Furthermore, control elements 42 and 43 are shown that allow rotation of the three-dimensional virtual master model 34 about the X and Y axes. The virtual master model 34 is processed by means of the virtual tools 37, 38, 39, 40, and 41 in order to correct malpositions of the patient's teeth and produce an ideal virtual setup model, in which all malpositions of the patient's teeth have been corrected. The necessary positional changes of the individual teeth can then be computed by the planning unit implementing deviations of the master model 34 from the corrected setup model. From the corrected positional changes of the individual teeth, the necessary corrective forces that must act on the teeth are determined by means of the planning unit while allowing for factors derived from the optical three-dimensional image, namely the spatial arrangement and shape of the teeth, and additional factors derived from the three-dimensional radiograph concerning the distribution of hard and soft tissue, namely the positions and dimensions of tooth roots in the apical base of a jaw, dimensions of the jawbone, anatomical limitations, the shape of the gingivae, the nasal floor, and the position of the palate, the known material constants of the different types of tissue and materials of the brackets 3 and arch 4 being implemented for purposes of computation. The manner in which the brackets 3 and arch 4 are to be configured in order to exert these necessary corrective forces on the patient's teeth 2 is computed in the next step by means of the planning unit. A probability of success 44 in achieving the desired permanent mechanical positional changes of the patient's teeth 2 according to the setup model is computed by the planning unit 30, for which purpose the known factors derived from the optical three-dimensional image and the three-dimensional radiograph and the known material constants of the different types of tissue and materials are implemented. If the probability of success 44 is too low, alternative recommendations for treatment such as extracting, stripping, or operating are suggested by the planning unit 30. In addition to the improvement of the planning method, the user can input individual treatment strategies, namely selected occlusal concepts such as bioesthetic or prosthetic care, the case history of the respective patient and overcompensation of the correction, if required, and these can be allowed for when planning the bracket system 1. For example, the material properties and positions of already known implant screws used for anchoring artificial teeth can be allowed for in the planning process. For anchoring teeth that do not require correction in terms of their position relative to the jaw, it is possible to use mini-screws that are attached to the palate so that the latter absorbs the corrective forces emerging on the brackets. The advantage of these mini-screws is that, unlike teeth, they are stable in terms of their position relative to the palate.

Figure 4:
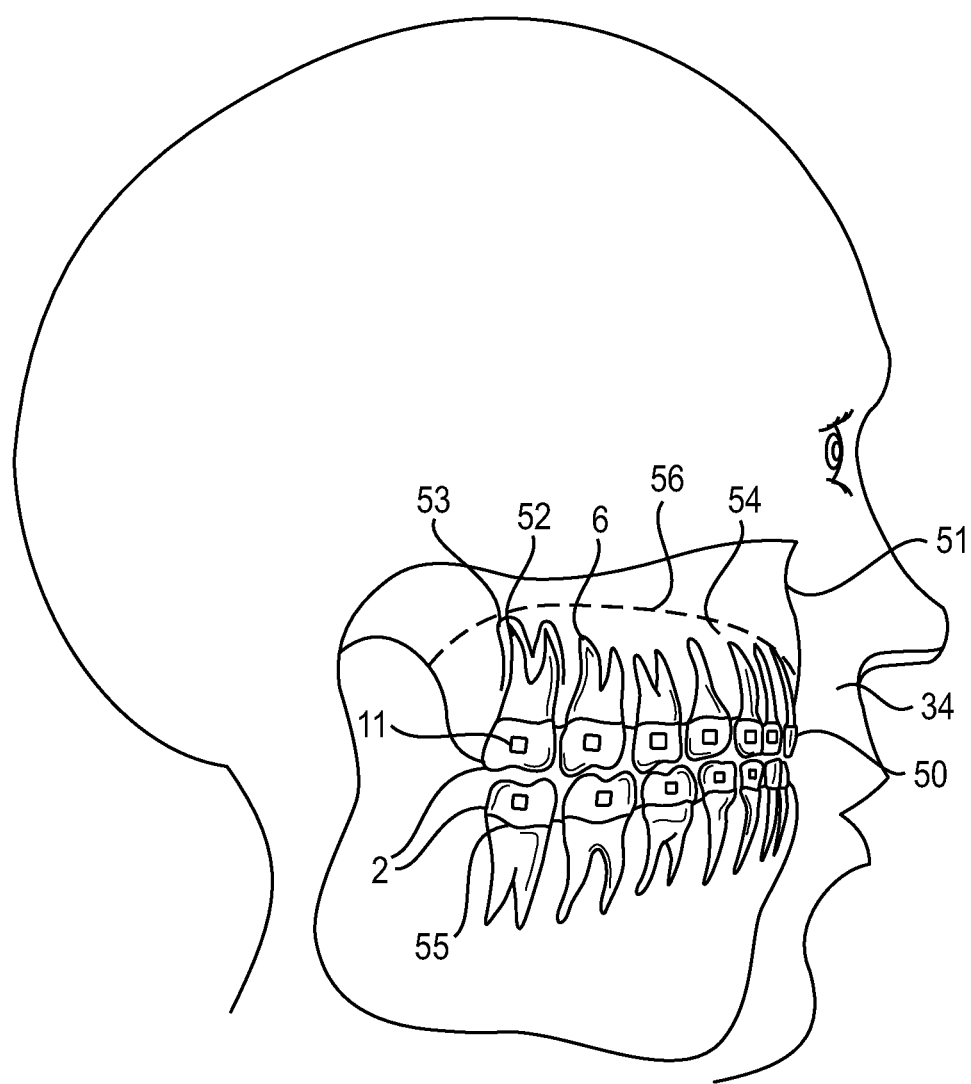
FIG. 4 is a sketch of a master model.

FIG. 4 is a sketch of the master model 34 shown in FIG. 3, the data of the three-dimensional optical image 50 being merged with the data of the three-dimensional radiograph 51 by means of superimposition of the registration points 11 of the platelets 6. In particular, factors derived from the optical three-dimensional image 50 such as the spatial arrangement and shape of the patient's teeth 2 and additional factors derived from the three-dimensional radiograph 51 concerning the distribution of hard and soft tissue, namely the positions and dimensions of tooth roots 52 in the apical base 53 of a jaw, the dimensions of the jawbone 54, the shape of the gingivae 55, additional anatomical limitations, the nasal floor, and the position of the palate 56 can be determined from the virtual master model 54. In this context, the position of the nasal floor is important for the correction of anterior teeth. FIG. 4 is a side view of the virtual master model that is displayed by the planning unit 30 on the monitor 31, as shown in FIG. 3.

Figure 5:
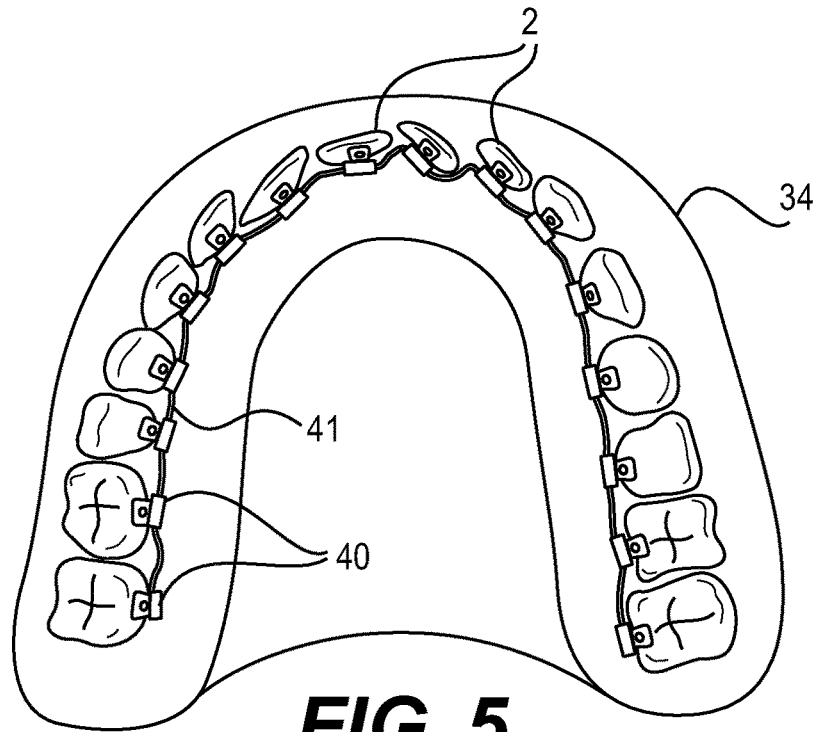
FIG. 5 is a sketch of the virtual master model shown in FIG. 3 and FIG. 4 showing malpositions of a patient's teeth.

FIG. 5 shows the virtual master model 34 shown in FIGS. 3 and 4 showing the malpositions of the patient's teeth 2. As shown in FIG. 3, the individual teeth 2 are corrected virtually by means of the planning unit 30 using the virtual tools 37, 38, 39, 40, and 41, so that a corrected ideal setup model is produced.

Figure 6:
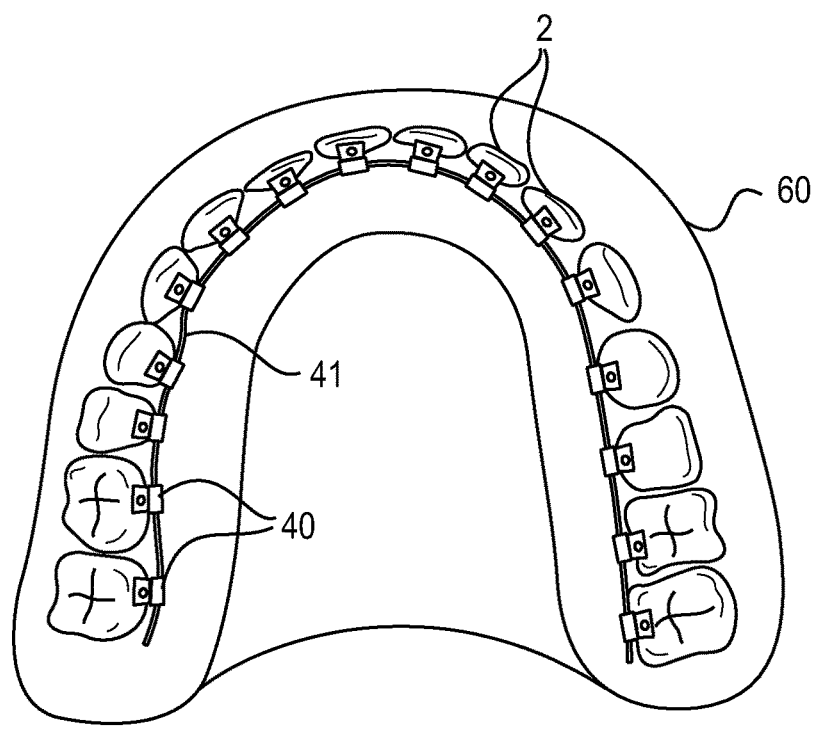
FIG. 6 is a sketch of a corrected ideal setup model.

FIG. 6 shows the corrected ideal setup model 60 that is produced virtually by the user by means of the planning unit shown in FIG. 3 from the virtual master model 34 shown in FIG. 5. In the setup model, all malpositions of the teeth 2 have been corrected in that the teeth have been rotated about their own axes by means of the virtual tool 37, altered in terms of their height by means of the virtual tool 38 and moved laterally by means of the virtual tool 39 in order to close any gaps between the teeth. The required corrective forces are determined by means of the planning unit 30 from the necessary positional changes of the individual teeth 2 resulting from a comparison of the master model 34 with the setup model 60, and the models 40 of the brackets 3 and the model 41 of the arch 4 are planned accordingly. The user can additionally input individual treatment strategies such as bioesthetic care, the case history of the respective patient, and overcompensation of the correction, if required, all of which can be allowed for when planning the models 40 of the brackets and the model 41 of the arch 4. From the known position of the bonded platelets 6 on the teeth 2 and the planned configuration of the models 40 of the brackets 3, the planning unit 30 determines the locations at which the bonding surfaces of the unprepared brackets are to be provided with a recess to match the platelet by means of a CAD/CAM unit.

Figure 7:
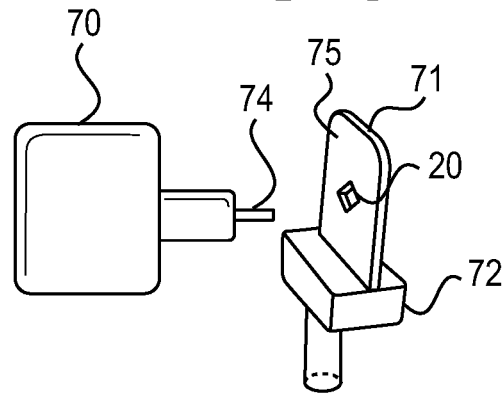
FIG. 7 is a sketch of a CAD/CAM unit for adapting an unprepared bracket.

FIG. 7 is a sketch of a CAD/CAM unit 70 that is implemented for adjusting an unprepared bracket 71. The unprepared bracket is secured on a holder, and a recess 20 planned by means of the planning unit 30 shown in FIG. 3 is carved out using a milling cutter 74. Furthermore, the entire bonding surface 75 of the unprepared prefabricated bracket 71 is processed by the milling tool 74 such that the bonding surface forms a mating surface for the respective tooth surface 5 that is to be bonded to the bracket 71. Thus a precise fit of the brackets 3 on the teeth 2 is achieved.

Figure 8A:
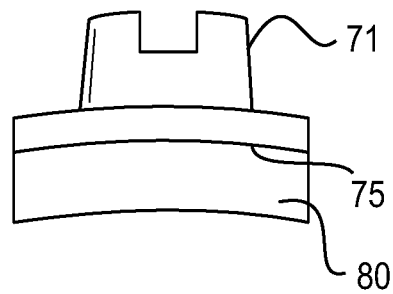
FIG. 8A is a sketch of an alternative unprepared bracket before the machining step.

FIG. 8A represents an alternative embodiment of a bracket 71 to be prepared, in which the bonding surface 75 is coated with a plastic layer 80.

Figure 8B:
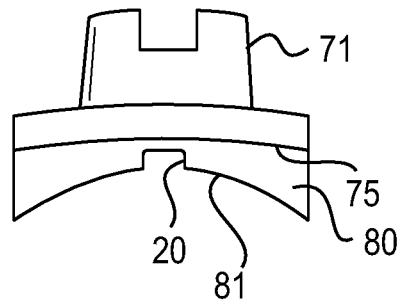
FIG. 8B is a sketch of an alternative unprepared bracket following the machining step.

FIG. 8B is a view of the bracket 71 shown in FIG. 8A following the machining method carried out by means of a milling cutter 74, as shown in FIG. 7. The plastic layer 80 is machined by means of the milling cutter 74 shown in FIG. 7 such that the processed surface 81 of the plastic layer 80 forms a mating surface for the respective tooth surface 5. Furthermore, a recess 20 is carved out of the layer 80 of plastics material to provide a precise fit of the recess on the respective platelet 6. As a result, the tool 74 has a longer service life than when used for machining metal, as shown in FIG. 7.

LIST OF REFERENCE NUMERALS OR CHARACTERS 1 bracket system
2 patient's teeth
3 bracket
4 arch
5 tooth surface
6 platelet
10 registration element
11 registration points
20 recess
30 planning unit
31 video monitor
32 keyboard
33 computer mouse
34 master model
35 virtual worktop
36 cursor
37 first tool
38 second tool
39 third tool
40 fourth tool
41 fifth tool
44 success probability
46 virtual tooth 50 three-dimensional optical image
51 three-dimensional radiograph
52 dental root
53 apical base
54 jawbone
55 gingiva
56 position of the palate
60 setup model
70 CAD/CAM unit
71 unprepared bracket
73 recess
74 milling cutter
75 bonding surface

The invention claimed is:

1. A dental bracket system, comprising:
a bracket that includes: (i) a bonding surface for adhesion to a surface of a tooth to be corrected, the bonding surface being an outer surface of the bracket, (ii) a recess formed in the bonding surface, and (iii) a slot on an opposite side of the bracket from the bonding surface;
an archwire with a cross-sectional diameter less than a width of the slot; and
a platelet that includes (i) a surface for adhesion to a surface of the tooth to be corrected, and (ii) at least one registration point in the form of a protuberance or a recess in an outer surface of the platelet on an opposite side of the platelet from the surface for adhesion,
wherein an entire outer periphery of the platelet fits within the recess formed in the bonding surface of the bracket.

2. The bracket system recited in claim 1, wherein the at least one registration point is formed from a material with an absorptivity for X-ray radiation that is different from an absorptivity for X-ray radiation of at least one other material from which the platelet is formed.

3. The bracket system recited in claim 1, wherein the at least one registration point is in the form of a protuberance from the outer surface of the platelet, and a base of the recess formed in the bonding surface of the bracket includes a depression which is a counterpart of the protuberance from the outer surface of the platelet.

4. The bracket system recited in claim 3, wherein the protuberance is in the shape of a round spherical segment.

5. The bracket system recited in claim 1, where the surface of the platelet includes a plurality of registration points in the form of protuberances from the outer surface of the platelet, and a base of the recess formed in the bonding surface of the bracket includes a plurality of depressions which are respective counterparts of the protuberances from the outer surface of the platelet.

6. The bracket system recited in claim 5, wherein the plurality of registration points are arranged as an equilateral triangle.

7. The bracket system recited in claim 1, further comprising:
a second bracket that includes (i) a second bonding surface for adhesion to a surface of another tooth to be corrected, the second bonding surface being an outer surface of the second bracket, (ii) a second recess formed in the second bonding surface, and (iii) a second slot on an opposite side of the second bracket from the second bonding surface; and
a second platelet that includes (i) a surface for adhesion to a surface of the other tooth to be corrected, and (ii) at least one registration point in the form of a protuberance or a recess in an outer surface of the second platelet on an opposite side of the platelet from the surface for adhesion to the surface of the other tooth,
wherein a relative location of the recess in the bonding surface of the bracket is different from a relative location of the second recess in the second bonding surface of the second bracket.

8. The bracket system recited in claim 7, wherein an orientation of the recess formed in the bonding surface of the bracket is different from an orientation of the second recess in the second bonding surface of the second bracket.

9. A dental bracket system, comprising:
a bracket that includes: (i) a bonding surface for adhesion to a surface of a tooth to be restored which is an outer surface of the bracket, and (ii) a recess formed in the bonding surface; and
a platelet that includes at least one registration point in the form of a protuberance or a recess in an outer surface of the platelet on an opposite side of the platelet from a side that includes a surface for adhesion to a tooth to be corrected, wherein an entire outer periphery of the platelet fits within the recess formed in the bonding surface of bracket.

10. The bracket system recited in claim 9, wherein the at least one registration point is in the form of a protuberance from the outer surface of platelet, and a base of the recess formed in the bonding surface of the bracket includes a depression which is a counterpart of the protuberance from the outer surface of the platelet.

11. The bracket system recited in claim 10, wherein the at least one registration point is in the shape of a round spherical segment.

12. The bracket system recited in claim 9, where the surface of the platelet includes a plurality of registration points in the form of protuberances from the outer surface of the platelet, and a base of the recess formed in the bonding surface of the bracket includes a plurality of depressions which are respective counterparts of the protuberances from the outer surface of the platelet.

13. The bracket system recited in claim 9, further comprising:
a second bracket that includes (i) a second bonding surface for adhesion to a surface of another tooth to be restored, the second bonding surface being an outer surface of the second bracket, and (ii) a second recess formed in the second bonding surface; and
a second platelet that includes at least one registration point in the form of a protuberance or a recess in an outer surface of the second platelet,
wherein a relative location of the recess in the bonding surface of the bracket is different from a relative location of the second recess in the second bonding surface of the second bracket.

14. The bracket system recited in claim 13, wherein an orientation of the recess formed in the bonding surface of the bracket is different from an orientation of the second recess in the second bonding surface of the second bracket.

15. A dental bracket system, comprising:
a bracket that includes: (i) a bonding surface for adhesion to a surface of a tooth to be corrected, the bonding surface being an outer surface of the bracket, (ii) a recess formed in the bonding surface, and (iii) a slot on an opposite side of the bracket from the bonding surface;
an archwire with a cross-sectional diameter less than a width of the slot; and
a platelet that includes (i) a surface for adhesion to a surface of the tooth to be corrected, and (ii) at least one registration point in the form of a protuberance or a recess in an outer surface of the platelet on an opposite side of the platelet from the surface for adhesion, wherein a periphery of the platelet fits within the recess formed in the bonding surface of the bracket.

16. The bracket system recited in claim 15, wherein the at least one registration point is formed from a material with an absorptivity for X-ray radiation that is different from an absorptivity for X-ray radiation of at least one other material from which the platelet is formed.

17. The bracket system recited in claim 15, wherein the at least one registration point is in the form of a protuberance from the outer surface of the platelet, and a base of the recess formed in the bonding surface of the bracket includes a depression which is a counterpart of the protuberance from the outer surface of the platelet.

18. The bracket system recited in claim 17, wherein the protuberance is in the shape of a round spherical segment.

19. The bracket system recited in claim 15, where the surface of the platelet includes a plurality of registration points in the form of protuberances from the outer surface of the platelet, and a base of the recess formed in the bonding surface of the bracket includes a plurality of depressions which are respective counterparts of the protuberances from the outer surface of the platelet.

20. The bracket system recited in claim 19, wherein the plurality of registration points are arranged as an equilateral triangle.

21. The bracket system recited in claim 15, further comprising:
a second bracket that includes (i) a second bonding surface for adhesion to a surface of another tooth to be corrected, the second bonding surface being an outer surface of the second bracket, (ii) a second recess formed in the second bonding surface, and (iii) a second slot on an opposite side of the second bracket from the second bonding surface; and
a second platelet that includes (i) a surface for adhesion to a surface of the other tooth to be corrected, and (ii) at least one registration point in the form of a protuberance or a recess in an outer surface of the second platelet on an opposite side of the platelet from the surface for adhesion to the surface of the other tooth,
wherein a relative location of the recess in the bonding surface of the bracket is different from a relative location of the second recess in the second bonding surface of the second bracket.

22. The bracket system recited in claim 21, wherein an orientation of the recess formed in the bonding surface of the bracket is different from an orientation of the second recess in the second bonding surface of the second bracket.

23. A dental bracket system, comprising:
a bracket that includes: (i) a bonding surface for adhesion to a surface of a tooth to be restored which is an outer surface of the bracket, and (ii) a recess formed in the bonding surface; and
a platelet that includes at least one registration point in the form of a protuberance or a recess in an outer surface of the platelet on an opposite side of the platelet from a side that includes a surface for adhesion to a tooth to be corrected, wherein a periphery of the platelet fits within the recess formed in the bonding surface of bracket.

24. The bracket system recited in claim 23, wherein the at least one registration point is in the form of a protuberance from the outer surface of platelet, and a base of the recess formed in the bonding surface of the bracket includes a depression which is a counterpart of the protuberance from the outer surface of the platelet.

25. The bracket system recited in claim 24, wherein the at least one registration point is in the shape of a round spherical segment.

26. The bracket system recited in claim 23, where the surface of the platelet includes a plurality of registration points in the form of protuberances from the outer surface of the platelet, and a base of the recess formed in the bonding surface of the bracket includes a plurality of depressions which are respective counterparts of the protuberances from the outer surface of the platelet.

27. The bracket system recited in claim 23, further comprising:
a second bracket that includes (i) a second bonding surface for adhesion to a surface of another tooth to be restored, the second bonding surface being an outer surface of the second bracket, and (ii) a second recess formed in the second bonding surface; and
a second platelet that includes at least one registration point in the form of a protuberance or a recess in an outer surface of the second platelet,
wherein a relative location of the recess in the bonding surface of the bracket is different from a relative location of the second recess in the second bonding surface of the second bracket.

28. The bracket system recited in claim 27, wherein an orientation of the recess formed in the bonding surface of the bracket is different from an orientation of the second recess in the second bonding surface of the second bracket.

* * * * *